United States Patent [19]

Koslow

[11] Patent Number: 4,829,007

[45] Date of Patent: May 9, 1989

[54] PROCESS FOR DETECTING A PLATEABLE METAL IN AN AQUEOUS FLUID

[76] Inventor: Ralf Koslow, 1 Horizon Rd., Apt. 1416, Fort Lee, N.J. 07024

[21] Appl. No.: 232,757

[22] Filed: Aug. 16, 1988

[51] Int. Cl.$^4$ ............................................. G01N 33/18
[52] U.S. Cl. ..................................... 436/80; 204/1 T; 436/73; 436/81; 436/83
[58] Field of Search ................... 204/1 T; 436/73, 77, 436/80, 81, 83, 84

[56] References Cited

PUBLICATIONS

Graeme E. Batley et al., Anal. Chem., vol. 49, No. 13, pp. 2031–2035, (1977).
P. E. Doherty et al., Anal. Chem., vol. 43, No. 13, pp. 1887–1888, (1971).
J. Kinard et al., Anal. Chem., vol. 46, No. 8, pp. 1106–1109, (1974).

Primary Examiner—G. L. Kaplan
Attorney, Agent, or Firm—Bernard Lieberman

[57] ABSTRACT

A process is provided for detecting trace amounts of a plateable metal in an aqueous fluid such as drinking water or industrial effluents. The process comprises an initial concentration step in an electrochemical plating cell whereby the metal in the fluid is deposited upon a glassy carbon plating electrode which is thereafter deplated in a second electrochemical cell wherein a porous solid test matrix impregnated with electrolyte is maintained proximate to the deplating electrode for retaining in solution the resulting metal ions formed from the deplated metal. A color indicator is then added to the test matrix to provide an indication of the presence of said metal.

14 Claims, No Drawings

PROCESS FOR DETECTING A PLATEABLE METAL IN AN AQUEOUS FLUID

BACKGROUND OF THE INVENTION

This invention relates to a method of detecting the presence of plateable metals in aqueous fluids, even when present at extremely low concentrations in such fluids. More particularly this invention relates to a highly sensitive method for detecting a plateable metal, such as lead, when present in trace amounts, as low as 5 parts per billion, in fluids such as drinking water, industrial effluents, body fluids and the like. For purposes of convenience, the method of the invention will be hereinafter described, for the most part, within the context of detecting lead as the plateable metal of interest, but it will be apparent from the description herein that the method of the invention is sufficiently broad in scope to enable the detection of a wide variety of other plateable metals including silver, gold, cadmium and chromium.

A continuing problem in the field of environmental protection relates to the detection of toxic metals such as lead, cadmium, arsenic, copper and the like in a wide variety of industrial effluent streams, rivers and reservoirs. While there are numerous known color spot tests for detecting lead, for example, they are generally ineffective for screening drinking water or industrial wastewater streams. This is because the concentration of lead in such fluids which is considered troublesome (often as low as 5 parts per billion) is ordinarily well below the detection limit of these spot tests; the lower limit of detection being generally about 2000 parts per billion. Thus, an initial concentration step is necessary before a conventional lead spot test can be used.

Solvent extraction with dithizone in chloroform or carbon tetrachloride is a known method of concentrating lead for spot testing. While this is considered to be a sensitive method of detection it suffers from the obvious drawback of having to use poisonous chemicals which are relatively unstable over a period of time. As a practical matter, the need to use materials such as cyanide and carbon tetrachloride precludes the general applicability of such method of detection to all but trained chemists.

Polarography and, in particular, anodic stripping voltametry (ASV) are known electrochemical methods of determining the presence of trace metals in various solutions. ASV relies on concentrating the metal of interest by cathodic deposition at an electrode (usually a hanging mercury drop electrode) under carefully controlled conditions for a known length of time. Following this concentration step, the metal is stripped from the electrode by scanning the voltage anodically to effect deplating at a voltage characteristic for the metal of interest while measuring the current-time transient. The height of the current peak corresponding to the area under the current-time curve is calibrated to provide a measure of the quantity of the metal of interest in the sample. U.S. Pat. No. 4,146,436 to Kellerman et al and U.S. Pat. No. 3,904,487 to Lieberman et al are illustrative of this electrochemical method of analysis.

While ASV is a quantative analytical technique which is highly sensitive for metal detection, it has inherent limitations for purposes of general applicability. It requires a skilled operator to carry out the method of analysis as well as expensive electrochemical equipment for effecting such polarographic technique. Consequently, ASV cannot be used by say, a layman, wishing to determine whether drinking water is free of metal contamination.

Accordingly, there is a need in the art for a highly sensitive but non-hazardous method of testing for the presence of certain plateable metals in aqueous fluids, which is semi-quantitative in nature, but nevertheless extremely useful for screening fluids such as drinking water or industrial effluent streams by relatively unskilled individuals and without the need for expensive electrochemical polarographic equipment.

SUMMARY OF THE INVENTION

The present invention provides a process for detecting the presence of trace amounts of a plateable metal in an aqueous fluid, said trace amounts corresponding to concentrations of said metal as low as five parts per billion in said fluid, comprising the steps of:

(a) providing an electrochemical plating cell containing in series connection (i) a direct current voltage source, (ii) a glassy carbon electrode as the negative plating electrode, (iii) a counter electrode as the positive anode and (iv) a sample portion of the fluid containing the metal to be detected, said plating electrode and said counter electrode being at least partially immersed in said fluid, (b) adding a buffer solution to said sample portion of fluid so as to adjust the pH to the desired value for metal plating as carried out in step (c);

(c) applying a constant negative voltage to the plating electrode relative to the counter electrode for a period of time sufficient to effect plating of at least a detectable amount of said metal upon the plating electrode, said detectable amount being the minimum amount of said metal which when transferred to a test matrix containing an appropriate color indicator is capable of causing a discernible color change;

(d) removing the glassy carbon electrode containing plated metal from said plating cell subsequent to step (c) and thereafter inserting same in an electrochemical deplating cell for anodic deplating, said deplating cell containing in series connection (i) a direct current voltage source, (ii) the plated glassy carbon electrode as the positive anode, (iii) a counter electrode as the negative cathode, (iv) a porous solid test matrix for retaining in solution the metal ions formed at the anode from the deplated metal, said test matrix being impregnated with an electrolyte solution to facilitate deplating of the metal as carried out in step (e), said anode and said cathode being each in direct contact with, and separated from each other by, said test matrix, said test matrix being maintained as an ionic conductive path between the two electrodes, said deplating cell containing no fluid or solution other than that contained within the pores of said test matrix;

(e) applying a constant positive voltage to the plated glassy carbon electrode relative to the counter electrode in said deplating cell so as to effect deplating of metal from said glassy carbon electrode, the resulting metal ions being substantially retained in solution within the pores of said test matrix; and thereafter (f) adding a color indicator for the metal to be detected to said test matrix to provide an indication of the presence of said metal.

The process of the present invention is, in essence, a three-step process. In the first step, the trace amounts of lead in the sample fluid are concentrated and collected by plating same onto a glassy carbon electrode in an electrochemical plating cell as described. The conditions of plating (e.g., time and current density) are selected so as to effect plating of at least 0.1 microgram of lead from the sample fluid, an amount of lead sufficient to provide a clear, discernible color change when such amount is transferred to a test matrix containing a color indicator for lead.

In the second step, the lead is electrochemically stripped or deplated from the electrode and the resulting ionic metal substantially transferred onto a small reaction zone in a porous test material or matrix which among other things, serves to retain the resulting ionic metal in the buffer or electrolyte solution contained within the pores. This may be conveniently carried out by simply reversing the polarity of the plated electrode so that it is at a positive potential relative to the counter electrode, and bringing such plated electrode into direct contact with the test matrix which is maintained as a conductive path between the two electrodes. This metal deplating step is characterized by the absence of any electrolyte or solution other than the solution contained within the porous test matrix.

In the third step, a color developer solution or indicator is added directly to the text matrix to produce a characteristic red color in the pores of the test matrix upon contact with ionic lead.

The prime advantage of the process of the invention is that it is able to be carried out by relatively unskilled individuals without the need for expensive electrochemical equipment. Metal concentration which is effected in the plating cell, and metal stripping carried out in the deplating cell require only relatively simple equipment: a glassy carbon (or vitreous carbon) electrode, a counterelectrode and a direct current voltage source such as a dry cell battery. While the process employs a conventional color indicator in the final step to determine the presence of lead, the overall sensitivity of the present process for detecting lead has been improved by two orders of magnitude relative to a conventional spot test. Thus, whereas the ordinary spot test for lead using a solution of sodium rhodizonate has a sensitivity for lead of about 2000 parts per billion, the process of the invention by virtue of its initial concentration and deplating steps, can detect lead at a level of about 5 parts per billion.

The process is broadly applicable to any metal which satisfies the following requirements: it can be electroplated from solution; it can be deplated anodically into a test matrix; and there exists a color developer or indicator which is specific for such metal. Among the metals which are suitable for detection in accordance with the process are the following: coinage metals, group IB; precious metals of the platinum group; group IIIB, IVB and VB metals. Preferred metals are lead, copper, cadmium, chromium, silver and gold.

DETAILED DESCRIPTION OF THE INVENTION

The electrochemical plating cell which serves to concentrate the lead from the sample fluid employs a glassy carbon electrode as the cathodic plating electrode. It is a non-porous form of carbon. The choice of such electrode is important because it has a high hydrogen evolution overvoltage. That is, it allows the electrode to be maintained at a sufficiently negative voltage so that lead plating can occur in preference to the hydrogen evolution reaction. The use of noble metals such as a platinum electrode results in a less efficient plating reaction and a significantly higher detection limit, namely, a less sensitive process for detecting lead.

Proper electrode pre-cleaning is important for efficient plating at the glassy carbon electrode. This is conveniently accomplished by abrading the surface of the electrode with a polishing solution, preferably a suspension of micron-sized particles of alumina, to provide a uniformly clean and shiny surface. The pre-cleaning step should remove all traces of previously plated metals which would otherwise cause a false positive result.

The counter electrode is preferably comprised of 300 series stainless steel. Its area is preferably greater than that of the plating electrode, and most preferably at least 10 times the electrode area of the plating electrode to inhibit lead deposition on the anode.

The buffer solution or electrolyte added to the sample fluid in the plating cell is preferably a one molar sodium acetate solution of pH about 4.5, added in a ratio of about one part buffer solution to 5 parts of the fluid sample, (e.g. drinking water, industrial effluent). Less prefered solutions include more dilute buffer solutions such as 10% or 5%, by weight, acetate buffer. The buffer solution is selected to provide the necessary pH and buffer capacity to hold lead in solution as the acetate complex, preventing precipitation as the hydroxide. The resistivity is 100 ohm-cm which is sufficient for uniform plating.

The current flow in the plating cell is set at about 20 to 40 milliamps per square centimeter which provides a sufficient amount of hydrogen evolution at the electrode surface to cause stirring. Higher current densities provide no advantage and result in a more rapid battery drain. A preferred negative potential for lead plating is $-2$ to $-3$ volts relative to a standard saturated calomel electrode (SCE).

The reaction time of the plating step in the electrochemical plating cell depends on the concentration of lead sought to be detected in the sample fluid. Generally, at least about 0.1 micrograms of lead need to be plated, such amount being approximately the minimum amount of lead which will cause a discernible color change when transferred to a test matrix containing a specific color indicator for lead. For the case of tap water where an analysis is required for traces of lead as low as 5 ppb, from about 6 to 24 hours of plating time is ordinarily required in an unstirred fluid, from about 8 to 16 hours being generally sufficient. Detection of lower levels of lead requires correspondingly longer plating times. If desired, the rate of lead deposition can be significantly increased by stirring the fluid sample, such by using a magnetic stirring bar and motor. However, for purposes of simplicity and for more reliable calibration of color change as a function of the approximate level of metal contaminants present in the fluid sample, it is preferred that plating is carried out in an unstirred fluid.

In the absence of mechanical stirring of the fluid sample, hydrogen evolution at the glassy carbon electrode during plating is desirable to promote lead deposition. Such gas evolution agitates the solution and brings a fresh supply of lead to the plating electrode surface. At the aforementioned electrode potential of $-2$ to $-3$ volts relative to SCE, sufficient hydrogen is evolved at the plating electrode to promote plating in a sodium acetate buffer solution of pH about 4.5.

Following the plating step, deplating may be carried out rapidly and conveniently. In accordance with a preferred embodiment, a porous solid test matrix is placed between the two electrodes and the potential of each reversed by reversing the probes of the direct current voltage source so that the glassy carbon electrode becomes the positive anode and the counter electrode becomes the cathode. A current flow for less than about 1 minute is ordinarily sufficient to effect deplating.

The test matrix is conveniently a porous blotting paper which absorbs sufficient electrolyte for conductivity and has sufficient pores to retain the metal precipitated during the color indicator reaction as a readily discernible colored spot or circle. Other suitable materials for the test matrix are fiber glass and porous polymeric materials such as nylon. To optimize the ability to discern the color change visually with the naked eye, the test matrix is preferably a white material.

The porous test matrix is impregnated with an electrolyte solution which serves two functions: it is a deplating electrolyte to facilitate the anodic deplating of lead and it serves as a buffer to maintain the pH at the value required to allow the color reaction to occur between the metal ions in the matrix and the color indicator. For lead deplating, a tartaric acid buffer of approximate pH 2.7 is used to impregnate the porous matrix. At this approximate pH, the color reaction of lead with a sodium rhodizonate solution is favored. Sodium rhodizonate is the preferred color indicator to react with lead.

EXAMPLE

Water containing about 25 parts per billion of lead was used as the test fluid to determine therein the presence of lead in accordance with the invention. The plating cell consisted of the following: a polished glassy carbon plating electrode, sealed in glass, having a diameter of 3 mm and a surface area of 0.07 square centimeters; a 300 series stainless steel counterelectrode having an area greater than 1 square centimeter; a series resistor of 1.5K ohm and a 9 volt alkaline transistor battery. The glassy carbon electrode was polished with a polishing suspension containing 0.3 micron-sized alumina.

A 150 ml beaker was filled with 100 ml of the sample water to be tested, to which there was added 20 ml of a buffer solution of one molar sodium acetate at pH of about 4.5. The two electrodes were placed in the beaker, the glassy carbon electrode being about ½ inch from the bottom of the beaker and about 1 inch from the counter electrode. The electrodes were connected to the battery through the 1.5K ohm resistor to complete the circuit. The negative probe was attached to the glassy carbon electrode. A voltage of −2.8 volts versus SCE was maintained at the plating electrode corresponding to a current of 2.5 milliamps or 36 milliamps per square centimeter. Bubbles were observed to rise briskly from the plating electrode. A plating time of about 20 hours was used after which the reaction was stopped and the glassy carbon electrode removed from the beaker.

Liquid adhering to the sides of the electrode was gently blotted off, care being taken not to contact the surface of the electrode so as to prevent inadvertent mechanical removal of lead. The battery and resistor were then arranged so that the polarity of the glassy carbon electrode was reversed, the positive pole of the battery now being connected to the glassy carbon electrode, and the negative pole connected to the stainless steel counter electrode. A square piece of blotter paper (one inch by one inch) was used as the solid porous test matrix by impregnating same with several drops of an electrolyte solution of sodium tartrate and tartaric acid at pH of about 2.7. The impregnated test matrix was then placed on the stainless steel electrode. The glassy carbon electrode was then placed gently against the test matrix, and a deplating current of 1.5 milliamps was allowed to flow corresponding to a voltage of +4 volts vs. SCE at the glassy carbon electrode. After about 10 seconds of current flow, the current was stopped and the test matrix was removed. One drop of orange-colored sodium rhodizonate solution was then added to the test matrix resulting in a violet red color forming by reaction with lead in the pores of the text matrix. The color persisted for 24 hours. The greater the amount of lead deposited, the more intense is the violet color allowing estimates of the amount of lead to be made with great accuracy.

As evidenced by the above, 5 parts per billion of lead in water can be detected by the process of the invention, allowing a significantly more sensitive means of detecting contaminants in water than is capable by color indicator tests known in the art.

What is claimed is:

1. A process for detecting the presence of trace amounts of a plateable metal in an aqueous fluid, said trace amounts corresponding to concentrations of said metal as low as five parts per billion in said fluid, comprising the steps of:
   (a) providing an electrochemical plating cell containing in series connection (i) a direct current voltage source, (ii) a glassy carbon electrode as the negative plating electrode, (iii) a counter electrode as the positive anode and (iv) a sample portion of the fluid containing the metal to be detected, said plating electrode and said counter electrode being at least partially immersed in said fluid;
   (b) adding a buffer solution to said sample portion of fluid so as to adjust the pH to the desired value for metal plating as carried out in step (c);
   (c) applying a constant negative voltage to the plating electrode relative to the counter electrode for a period of time sufficient to effect plating of at least a detectable amount of said metal upon the plating electrode, said detectable amount being the minimum amount of said metal which when transferred to a test matrix containing an appropriate color indicator is capable of causing a discernible color change;
   (d) removing the glassy carbon electrode containing plated metal from said plating cell subsequent to step (c) and thereafter inserting same in an electrochemical deplating cell for anodic deplating, said deplating cell containing in series connection (i) a direct current voltage source, (ii) the plated glassy carbon electrode as the positive anode, (iii) a counter electrode as the negative cathode, (iv) a porous solid test matrix for retaining in solution the metal ions formed at the anode from the deplated metal, said test matrix being impregnated with an electrolyte solution to facilitate deplating of the metal as carried out in step (e), said anode and said cathode being each in direct contact with, and separated from each other by, said test matrix, said test matrix being maintained as an ionic conductive path between the two electrodes, said deplating cell containing no fluid or solution other than that contained within the pores of said test matrix;

(e) applying a constant positive voltage to the plated glassy carbon electrode relative to the counter electrode in said deplating cell so as to effect deplating of metal from said glassy carbon electrode, the resulting metal ions being substantially retained in solution within the pores of said test matrix; and thereafter (f) adding a color indicator for the metal to be detected to said test matrix to provide an indication of the presence of said metal.

2. A process in accordance with claim 1 wherein the platable metal to be detected is selected from the group consisting of lead, copper, cadmium, chromium, silver and gold.

3. A process in accordance with claim 2 wherein said plateable metal is lead.

4. A process in accordance with claim 3 wherein the first buffer solution added in step (b) is about a one molar sodium acetate solution of pH about 4.5.

5. A process in accordance with step 4 wherein said buffer solution is added in the ratio of about one part of buffer solution to 5 parts of said fluid.

6. A process in accordance with claim 3 wherein said second buffer solution which is absorbed in said test material is a solution of tartaric acid and sodium tartrate.

7. A process in accordance with claim 3 wherein the color indicator added to the test matrix in step (f) to detect the presence of lead is a solution of sodium rhodizonate.

8. A process in accordance with claim 2 wherein the time of plating in step (c) is from about 8 to 16 hours.

9. A process in accordance with claim 2 wherein the time of plating in step (c) is sufficient to plate at least 0.1 micrograms of lead.

10. A process in accordance with claim 2 wherein prior to plating in step (c) the glassy carbon electrode is cleaned by contacting its surface with a polishing liquid so as to abrade the surface of the electrode sufficiently to provide a clean surface for plating.

11. A process in accordance with claim 10 wherein said polishing liquid contains micron-sized alumina in suspension.

12. A process in accordance with claim 1 wherein said porous test matrix is comprised of porous paper or fiber glass.

13. A process in accordance with claim 1 wherein the counter electrode in said electromechanical plating cell is comprised of stainless steel.

14. A process in accordance with claim 1 wherein the counter electrode in said electrochemical deplating cell is comprised of stainless steel.

* * * * *